United States Patent [19]

Bunning et al.

[11] Patent Number: 4,593,127
[45] Date of Patent: Jun. 3, 1986

[54] HYDROFORMYLATION PROCESS

[75] Inventors: Donald L. Bunning, South Charleston; Michael A. Blessing, Sissonville, both of W. Va.

[73] Assignee: Union Carbide Corporation, Danbury, Conn.

[21] Appl. No.: 690,912

[22] Filed: Jan. 11, 1985

[51] Int. Cl.⁴ .......................................... C07C 45/50
[52] U.S. Cl. ...................................................... 568/454
[58] Field of Search ................................. 568/454, 451

[56] References Cited

U.S. PATENT DOCUMENTS

| | | | |
|---|---|---|---|
| 3,527,809 | 9/1970 | Pruett et al. | 568/454 |
| 4,148,830 | 4/1979 | Pruett et al. | 568/454 |
| 4,247,486 | 1/1981 | Brewester et al. | 568/454 |
| 4,283,562 | 8/1981 | Billig et al. | 568/454 |
| 4,298,541 | 11/1981 | Oswald et al. | 260/429 R |
| 4,400,548 | 8/1983 | Abatjoglou et al. | 568/454 |
| 4,482,749 | 1/1984 | Dennis et al. | 568/454 |
| 4,496,768 | 1/1985 | Dennis et al. | 568/454 |

FOREIGN PATENT DOCUMENTS

| | | | |
|---|---|---|---|
| 0016285 | 10/1980 | European Pat. Off. | 568/454 |
| 0016286 | 10/1980 | European Pat. Off. | 568/454 |
| 0096986 | 12/1983 | European Pat. Off. | 568/454 |
| 0096987 | 12/1983 | European Pat. Off. | 568/454 |
| 0096988 | 12/1983 | European Pat. Off. | 568/454 |
| 3102281 | 1/1982 | Fed. Rep. of Germany . | |
| 3245883 | 6/1984 | Fed. Rep. of Germany | 568/454 |
| 3245883 | 6/1984 | Fed. Rep. of Germany | 568/454 X |
| WO80/1690 | 8/1980 | PCT Int'l Appl. | 568/454 |

Primary Examiner—Werren B. Lone
Attorney, Agent, or Firm—Reynold J. Finnegan

[57] ABSTRACT

In a primary process for hydroformylating olefins to form aldehydes in which a liquid or gas recycle step is conducted and a gaseous effluent is vented, the improvement which comprises employing the effluent as a reactant feed for a decoupled secondary liquid-or gas recycle hydroformylation process conducted conjointly therewith.

24 Claims, 2 Drawing Figures

HYDROFORMYLATION PROCESS

BACKGROUND OF THE INVENTION

This invention relates to an improved process for hydroformylating an olefin with carbon monoxide and hydrogen in the presence of a rhodium catalyst.

Methods for producing aldehydes by the hydroformylation of an olefinically unsaturated organic compound with carbon monoxide and hydrogen in the presence of a rhodium-phosphorus complex catalyst and free phosphorus ligand are well known in the art as seen; e.g. by the basic low pressure oxo hydroformylation process of U.S. Pat. No. 3,527,809 and the rhodium-catalyzed liquid recycle hydroformylation process of U.S. Pat. No. 4,148,830.

In U.S. Pat. No. 4,148,830 issued Apr. 10, 1979, (the '830 Patent) it is disclosed that catalyst life can be enhanced and product yield improved by employing as a catalyst solvent for rhodium-catalyzed hydroformylation (or the "oxo" process), higher boiling aldehyde condensation products as defined therein. It was also found that the rhodium catalyst could be continuously or intermittently recycled to the hydroformylation reaction zone without significant loss of rhodium, catalyst life, reaction rates and efficiency.

Accordingly, the '830 Patent disclosed that liquid effluent from the reaction zone containing catalyst, solvent and gases, is processed to strip and recover the aldehyde product. During this procedure some hydrogen, carbon monoxide, unreacted olefin, and other by-product and inert gases dissolved in the reactor effluent are removed by reducing pressure on the effluent stream to flash off such gases. The desired aldehyde product is then recovered from said effluent and the liquid residue fraction of unrecovered aldehydic product, catalyst and high boiling condensation product is recycled to the reactor. Accordingly, this process has sometimes been referred to as a liquid-recycle hydroformylation process (or "liquid recycle process").

U.S. Pat. No. 4,247,486, issued Jan. 27, 1981 (the '486 Patent), discloses a hydroformylation process which is directed to further modifications of the basic oxo process disclosed in U.S. Pat. Nos. 3,527,809 and 4,148,830.

In this process, unreacted feed, the aldehyde reaction product and higher boiling condensation products, inter alia, are allowed to distill out of the reaction medium. The aldehyde product and condensation products are condensed from the gas recycle stream and unreacted feed contained therein (i.e., syn gas and olefin) are recycled to the reaction zone. This process is a gas recycle hydroformylation process or, simply, "a gas-recycle process."

U.S. Pat. No. 4,247,486 discloses that a by-product of such a recycle hydroformylation process is saturated alkane formed by the hydrogenation of the olefin. Thus, for example, propane is a by-product in the hydroformylation of propylene. Accordingly, a purge stream is taken from a gas recycle stream therein to remove such propane and to control its concentration within the process. The purge stream also contains, inter alia, aldehyde product, unreacted olefin, inert gases, as well as carbon monoxide and hydrogen. It is said in the '486 Patent that the recovery of olefin from such a stream is impractical and that the purge stream is typically used as a fuel.

Likewise, to control total reactor pressure in a liquid recycle process due to build up of inerts and the like, a gaseous purge is generally taken from the liquid recycle hydroformylation reactor, where excess hydrogen, carbon monoxide, unreacted olefin, inerts and alkane by-products, such as propane, are vented as off-gases.

In addition, during the product separation step in a liquid recycle process, some gases, primarily unreacted olefin and alkane by-product, which remain dissolved in the liquid catalyst-containing effluent, are separated along with the desired aldehyde product. A portion of such separated gases are condensed with the desired aldehyde product. The remaining separated gases can be purged from the system.

The amount of olefin and syn gas components lost by purging in such recycle processes can amount to a significant economic disadvantage over the life of a commercial continuous operation due to the efficiency loss of such purged desirables as unreacted olefin and syn gas.

In German Pat. No. 3,102,281, issued Dec. 23, 1982, a cobalt-catalyzed high pressure hydroformylation of propylene was conducted and the waste gas, resulting from the decobalting of the reaction mix, containing propylene, carbon monoxide and hydrogen, was introduced into a low pressure rhodium catalyzed hydroformylation process, simultaneously conducted. In German Laid-Open Patent No. 3,245,883, published June 14, 1984, flue gas from a low pressure rhodium hydroformylation process containing propylene is compressed and introduced into a high pressure cobalt catalyzed reactor for conversion to aldehyde.

SUMMARY OF THE INVENTION

In a primary liquid recycle or gas recycle rhodium-catalyzed hydroformylation process for producing aldehydes, wherein an olefin, carbon monoxide and hydrogen are reacted in the presence of a solubilized rhodium-phosphorous complex catalyst, free phosphorus ligand and higher boiling aldehyde condensation by-products to produce an aldehyde product, wherein a gaseous effluent comprising unreacted olefin and any of said aldehyde product, hydrogen, carbon monoxide and an alkane by-product is vented from the process, the improvement which comprises: conducting a decoupled secondary liquid recycle or gas recycle rhodium-catalyzed hydroformylation process conjointly with said primary process, wherein said gaseous effluent together with make-up carbon monoxide and hydrogen is employed as the reactant feed to the secondary process.

In the present invention a low pressure hydroformylation process is provided with significantly reduced physical losses of valuable compounds, e.g. olefin and syn gas, and with enhanced process flexibility.

The present invention provides for operating two or more low pressure oxo (LPO) reactors in a "decoupled" series mode, with separate catalyst solutions and separate product removal steps for each reactor.

There are important advantages to the decoupled series reaction system. As noted, in a typical primary recycle oxo process, gaseous purges utilized to control total reactor pressures and/or remove saturated olefin by-product to prevent its build-up in the system, result in discarding valuable olefin feed and syn gas, which is also present in the gaseous purge stream.

It has now been found that such a purge stream can be employed as a feed stream in a second "decoupled" low pressure hydroformylation process employing a gas or a liquid recycle. The decoupled process of this invention requires its own independent catalyst system and independent product recovery system. It is a key feature of this invention that unreacted olefin contained in a vent stream from the primary system can be employed as the sole olefin feed to the decoupled secondary hydroformylation process, i.e. make-up quantities of olefin need not be added to the decoupled hydroformylation process. Improvements in overall aldehyde conversions and efficiencies may be increased from 2 to 10% or more employing the present inventive decoupled series system, as compared to a conventional hydroformylation system.

In a continuous rhodium-catalyzed hydroformylation process with a liquid recycle, use of a decoupled series reactor can permit more precise control over catalyst values, reaction parameters and operating conditions to obtain higher process performance. Since high reaction rates are not required in the decoupled reactor in view of the lower concentration of olefin in the feed, one can employ used catalyst from a primary reaction system in the decoupled reactor. This feature prolongs catalyst life and enhances the economics of the process.

Independent reaction catalyst systems and independent product removal systems also provide increased operating flexibility. Turndown capabilities for such a process are very broad, since either of the separate systems could be completely shut down for maintenance, modifications or the like and the remaining system run at a reduced rate. In addition, since the "decoupled system" operates at higher olefin and syn gas utilization efficiency, then by increasing olefin concentration, the production capacity can be increased more than would be economically attractive with a simple dependent "coupled" series system in which the catalyst and product recovery are shared.

Increased operating flexibility is obtained since there is separate product recovery capability for each reactor. Each reactor can also be operated independently. Since the two reactor units in the "decoupled series" of this invention can be operated independently of one another as two separate units, two different aldehyde product mixtures, (i.e., having different normal to branched isomer aldehyde product ratios) can be produced at the same time without significant cross-contamination.

If desired, the decoupled series reaction units could be run with a mixed olefin feedstock, such as a mixed butene feedstock, with the catalyst in the first reactor being appropriate to react the alpha-olefin, selectively, and the catalyst in the secondary decoupled reactor being designed to convert the internal olefin.

The ability of the system to handle upsets is also improved. Undesired sudden increases in the flow of inerts through the system (such as a drop in feed purity) would present less of a problem. In addition, the "decoupled series" system suffers less penalty due to catalyst poisoning or inhibition, since the catalyst solutions are independent.

DETAILED DESCRIPTION OF THE INVENTION

Figure 1:
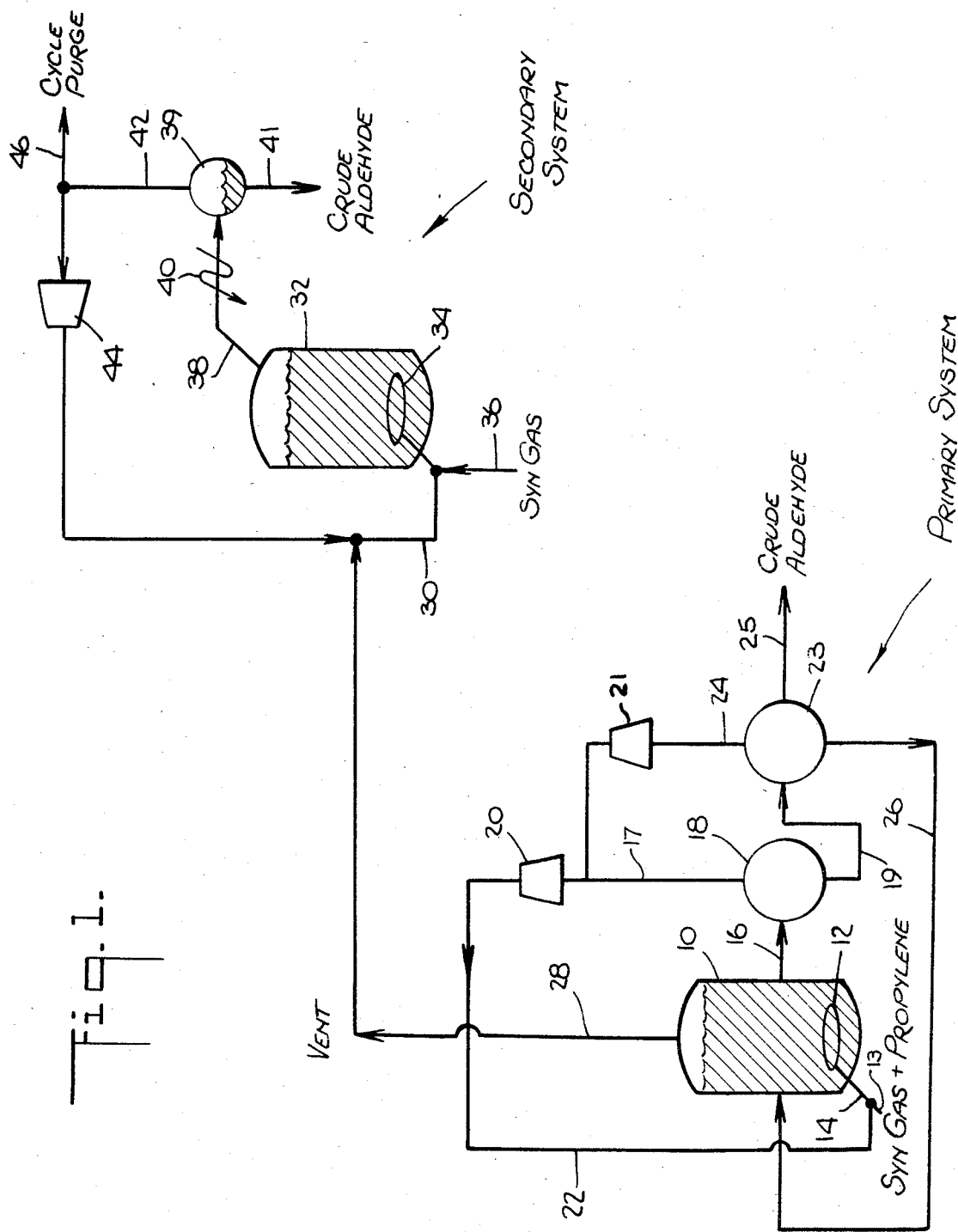
FIG. 1 is a schematic flow diagram of a primary single stage LPO liquid recycle process in which a gas vent from the primary reactor acts as a feed to a secondary decoupled LPO process employing a single stage reactor with a gas recycle.

This invention is applicable to improving any conventional continuous liquid recycle or gas recycle rhodium-phosphorus complex catalyzed hydroformylation process for producing aldehydes, which process is conducted in the presence of free organic phosphorus ligand. Such oxo processes and the conditions thereof are well known in the art as illustrated, e.g. by the continuous liquid recycle process of U.S. Pat. No. 4,148,830 and the continuous gas recycle process of U.S. Pat. No. 4,247,486. Such hydroformylation processes in general involve the production of aldehydes by reacting an olefinic compound with hydrogen and carbon monoxide gas in a liquid reaction medium which contains a soluble rhodium-phosphorus complex catalyst, free organophosphorus ligand and higher boiling aldehyde condensation by-products.

Of course it is to be understood that the particular manner in which the hydroformylation reaction is carried out and particular hydroformylation reaction conditions employed in either the primary system or the secondary system are not critical to the subject invention and may be varied widely and tailored to meet individual needs and produce the particular aldehyde product desired.

It should also be understood that the makeup of the hydroformylation media and reaction conditions in the primary and secondary system can be the same or different. Accordingly, the olefinic starting material reactants encompassed by the process of this invention can be terminally or internally unsaturated and be of straight-chain or branched-chain structure. Such olefins preferably contain from 2 to 5 carbon atoms.

Illustrative olefins are ethylene, propylene, 1-butene, 1-pentene, 2-butene, 2-methyl propene (isobutylene), isoamylene, 2-pentene, 2-methyl-1-butene and 2-methyl-2-butene. Of course, it is understood that mixtures of different olefinic starting materials can be employed, if desired, by the hydroformylation process of the subject invention. More specifically, the secondary system can be dedicated to hydroformylating a different olefin from that designated to be hydroformylated in the primary system. Among the more preferred olefins are propylene, 1-butene, 2-butene (cis or trans), isobutene and mixtures thereof. The most preferred olefin is propylene.

Likewise, any conventional rhodium-phosphorus complex catalyst can be employed and such catalysts as well as methods for their preparation are well known in the art. Such rhodium-phosphorus complex catalysts may include any rhodium-organophosphorus complex, such as the rhodium-organophosphine or rhodium-organophosphite complex hydroformylation catalysts heretofore advanced for such hydroformylation processes. Of course, mixtures of such catalysts can also be employed, if desired. Moreover, it is clear that the amount of complex catalyst present in the reaction medium of a given process need only be that minimum amount necessary to provide the rhodium metal concentration desired to be employed and which will furnish the basis for at least that catalytic amount of rhodium metal necessary to catalyze the particular hydroformylation process desired. In general, rhodium metal concentrations in the range of from about 10 ppm to about 1000 ppm, calculated as free metal, should be sufficient for most hydroformylation processes. It is generally preferred to employ from about 10 to 700 ppm of rhodium, and more preferably, from 25 to 500 ppm of rhodium, calculated as free metal.

As noted above, the hydroformylation process of this invention is carried out in the presence of free phosphorus ligand, i.e. ligand that is not complexed with the rhodium complex catalyst employed. However, while it is generally preferred that the free phosphorus ligand be the same as the phosphorus ligand of the rhodium-phosphorus complex catalyst, such is not necessary and different ligands can be employed in a given process, if desired. Acccordingly, as in the case of the rhodium-organophosphorus complex catalyst, any conventional organophosphorus ligand can be employed as the free ligand and such ligands, as well as methods for their preparation, are well known in the art. Such free phosphorus ligands may include any of the organophosphine or organophosphite ligands heretofore advanced for such hydroformylation processes. Of course, mixtures of such ligands can also be employed, if desired. Thus, the hydroformylation process of this invention may be carried out in any excess amount of free phosphorus ligand, e.g. at least one mole of free phosphorus ligand per mole of rhodium metal present in the reaction medium. The amount of free phosphorus ligand employed, in general, merely depends upon the aldehyde product desired, and the olefin and complex catalyst employed. Accordingly, amounts of free phosphorus ligand present in the reaction medium ranging from about 1 to about 300 or more per mole of rhodium present should be suitable for most purposes. For example, in general, large amounts of free triarylphosphine ligand, e.g. triphenylphosphine, such as more than 50 moles or, more preferably, more than 100 moles of free ligand per mole of rhodium have preferably been employed to achieve satisfactory catalytic activity and/or catalyst stabilization, while other phosphorus ligands, e.g. alkylarylphosphines and cycloalkylarylphosphines may help provide acceptable catalyst stability and reactivity without unduly retarding the conversion rates of certain olefins to aldehydes when the amount of free ligand present in the reaction medium is as little as 1 to 100 and, more preferably, 15 to 60 moles per mole of rhodium present.

More particularly, illustrative rhodium-phosphorus complex catalysts and illustrative free phosphorus ligands include, e.g. those disclosed in U.S. Pat. Nos. 3,527,809; 4,148,830; 4,247,486; 4,283,562; 4,400,548; 4,482,749; European Patent Applications, Publication Nos. 96,986; 96,987 and 96,988 (all published Dec. 28, 1983); PCT patent application, Publication No. WO 80/01690 (published Aug. 21, 1980) and U.S. Applications Ser. Nos. 581,352, filed Feb. 17, 1984 and 685,025, filed Dec. 28, 1984. Among the more preferred ligands and complex catalysts that may be mentioned are, e.g. the triphenylphosphine ligand and rhodium-triphenylphosphine complex catalysts of U.S. Pat. Nos. 3,527,809 and 4,148,830 and 4,247,486; the alkylphenylphosphine and cycloalkylphenylphosphine ligands, and rhodium-alkylphenylphosphine and rhodium-cycloalkylphenylphosphine complex catalysts of U.S. Pat. No. 4,283,562; and the dliorganophosphite ligands and rhodium-diorganophosphite complex catalysts of U.S. Applications Ser. Nos. 581,352 filed Feb. 17, 1984, and 685,025, filed Dec. 28, 1984. The the most preferred ligand is triphenylphosphine (TPP), while the preferred catalyst is a rhodium-TPP complex.

As further noted above, the hydroformylation reaction is carried out in the presence of higher boiling aldehyde condensation by-products. It is the nature of such continuous hydroformylation reactions employable herein to produce such higher boiling aldehyde by-products (e.g. dimers, trimers and tetramers) in situ during the hydroformylation process as explained more fully, e.g. in U.S. Pat. Nos. 4,148,830 and 4,247,486. Such aldehyde by-products provide an excellent carrier for the liquid catalyst recycle process. Indeed, while one may employ, if desired, any suitable solvent at the start up of a continuous process (aldehyde compounds corresponding to the desired aldehyde products being preferred), the primary solvent will normally eventually comprise both aldehyde products and higher boiling aldehyde condensation by-products due to the nature of such continuous process. Of course, aldehyde condensation by-products can also be preformed if desired and used accordingly. It is also obvious that the amount of such higher boiling aldehyde by-products present in the reaction medium may vary over wide limits and is generally governed only by equipment constraints and the particular aldehyde product to be produced. For example, initially the hydroformylation reaction can be effected in the absence or in the presence of small amounts of higher boiling aldehyde condensation by-products as a solvent for the rhodium complex catalyst, or the reaction can be conducted in the presence of upwards of 70 weight percent, or even as much as 90 weight percent, and more of such condensation by-products, based on the total liquid reaction medium. In general, ratios of aldehyde to higher boiling aldehyde condensation by-products within the range of from about 1.4 to about 20:1 by weight should be sufficient for most purposes. Likewise it is to be understood that minor amounts of other conventional organic co-solvents may be present if desired.

While the hydroformylation reaction conditions may vary over wide limits, as discussed above, in general it is more preferred that the process be operated at a total gas pressure of hydrogen, carbon monoxide and olefinic unsaturated starting compound of less than about 450 psia and more preferably less than about 350 psia. The minimum total pressure of the reactants is not particularly critical and is limited mainly only by the amount of reactants necessary to obtain a desired rate of reaction. More specifically, the carbon monoxide partial pressure of the hydroformylation process of this invention is preferably from about 1 to about 120 psia and, more preferably, from about 3 to about 90 psia, while the hydrogen partial pressure is preferably about 10 to about 160 psia and more preferably from about 15 to about 100 psia. In general $H_2$:CO molar ratio of gaseous hydrogen to carbon monoxide may range from about 1:10 to 100:1 or higher, the more preferred hydrogen to carbon monoxide molar ratio being from about 1:1 to about 50:1.

Further, as noted above, the hydroformylation process of this invention may be conducted at a reaction temperature from about 50° C. to about 145° C. However, in general, hydroformylations at reaction temperatures of about 60° C. to about 120° C. and more preferably about 75° C. to about 115° C. are preferred.

In one embodiment of this invention, the hydroformylation process employed in either the primary or secondary system can involve a continuous liquid recycle. In the continuous liquid recycle, a portion of the liquid reaction aldehyde product solution containing aldehyde product, solubilized rhodium-phosphorus complex catalyst, free phosphorus ligand and higher boiling aldehyde condensation by-products is removed from the reactor. The desired aldehyde product is separated via vaporization or distillation, in one or more stages, under normal, reduced or elevated pressure from the liquid reaction solution. The aldehyde product is condensed and collected in a product receiver, and further purified if desired. The remaining non-volatilized catalyst-containing liquid reaction production solution is recycled back to the reactor. Such types of continuous hydroformylation systems and methods for carrying them out are well known in the art and thus need not be particularly detailed herein.

In a preferred embodiment employing a liquid recycle step in the primary system, a solution of rhodium species catalyst in high boiling liquid condensation products with aldehydic products resulting from hydroformylation, syn gas, inerts, saturated olefinic by-products and the like is continuously or intermittently recycled to the hydroformylation zone. The solution is removed from the reactor at a rate sufficient to keep a relatively constant level of liquid in the reactor. The pressure on the effluent stream is then reduced to flash-distill off light gaseous hydroformylation products, including some unreacted olefin, hydrogen, saturated olefin by-products and the like. The flashed off-gases are compressed and returned to the reactor. Of course it is to be understood that such an intermediate step as said flash-distillation and return of the off-gases to the reactor is not critical to the process and can be omitted, if desired. Alternatively said off-gases can merely be purged, if desired. For example, said flash distillation intermediate step and return of said off-gas to the reactor may or may not be of any great benefit to a secondary system employing a liquid recycle process.

The effluent stream is then fed to a product separation zone wherein the crude aldehyde product is recovered by conventional techniques, e.g., distillation. Undissolved light gases are also vented off in the product separation zone and are returned to the reactor. Again, these off-gases may be merely purged, if desired, and such may be the case in the secondary system.

The remaining concentrated catalyst is recycled as a liquid stream to the reaction zone. Make-up syn gas and olefin are fed into the reaction medium, as required. In refining of the crude aldehyde, it is further preferred to recycle the light gases dissolved in the crude product to the reactor after their removal via conventional techniques; e.g. distillation, although they too may be wasted, if desired.

In this preferred embodiment of a primary liquid recycle process, a vent line is provided in the head space above the liquid level in the primary reactor to control the internal pressure build-up in the reactor and as the means for conveying the unreacted olefin feed to the secondary decoupled reactor. In the case of the secondary system employing a liquid recycle process this vent line from the headspace of the reactor can serve as the purge line for controlling internal pressure build-up in the secondary reactor.

It should be understood that the olefin starting material for the secondary decoupled system can be taken from any gaseous stream which could be vented from the primary process as off-gas. While such olefin starting material for the secondary decoupled process can be derived from any appropriate gas vent containing unreacted olefin and incidental alkane by-products taken from any suitable location in the primary reaction system, it is preferred to employ the vent stream from either the reactor headspace and/or from the product separation step as the feed for the secondary decoupled rhodium-catalyzed hydroformylation process. In the secondary process, olefin-containing vented gas from the primary system is admixed with make-up syn gas and the resulting feed is introduced into the reactor of the secondary system which contains a catalyst system of the present invention. Reaction products are removed and recovered employing a gas recycle or a liquid recycle step of this invention.

The process carried out in the secondary decoupled system, as set forth previously, can employ the same or different reaction conditions as utilized in the primary hydroformylation process discussed above. A liquid recycle or gas recycle can be employed in the secondary process in accordance with the same or different conditions as noted hereinbefore.

Accordingly, one embodiment of this invention can be further illustrated by reference to FIG. 1 which schematically shows a diagrammatic flowsheet suitable for practicing this invention.

Referring to FIG. 1, a stainless steel reactor 10 is provided with a sparger 12 having holes for providing a sufficient gas flow of olefin and synthesis gas. Additional spargers may be employed depending upon the size of the reactor, if desired. In the system illustrated, propylene is converted to butyraldehyde. A feed line 13 supplies make-up propylene and syn gas. An impeller (not shown) is employed to mix the reactor contents. An internal or external cooler (not shown) is employed to help control reaction temperature. A liquid effluent stream is removed via line 16 to a flash evaporator 18, wherein light gaseous hydroformylation components are vaporized, conducted through line 17 to compressor 20, compressed therein and recycled to the reactor via line 22 and feed line 14. The remaining liquid effluent is then passed via line 19 to a product removal zone 23.

In the product removal zone 23 which generally comprises a vaporizer/separator, aldehyde product is vaporized out of the catalyst stream via line 25 and, thereafter condensed and refined. Some olefin, syn gas and other gases dissolved in the catalyst stream are distilled off. A portion of the distilled-off gases are condensed with the aldehyde and said gases can be recovered during refining of the crude aldehyde product and recycled to the reactor (not shown). However, a significant portion of said distilled-off gases; e.g. the olefin, is not condensed with the aldehyde product, but is removed in a purge or vent stream 24 which is compressed in compressor 21 and recycled to line 22. The concentrated catalyst from the product removal step is recycled to the reactor via line 26.

In FIG. 1 a vent line 28 originating in the reactor headspace conducts unconverted olefin and syn gas to inlet line 30 of secondary decoupled reactor 32. Reactor 32 may be equipped in the same manner as reactor 10, e.g. sparger 34, agitator, inlet syn gas feed line 36, and means for temperature control.

The decoupled reactor 32 has an effluent line 38 to conduct gaseous effluents containing aldehyde product to a dedicated product recovery zone. A condenser 40 is utilized to condense the aldehyde product from the effluent gases. A separator-catchpot 39 is used to separate the condensed, crude aldehyde product from the non-condensed effluent gases. Gaseous materials are passed via line 42 to a compressor 44 and they recycled to inlet line 30 for reintroduction into the reactor. A purge line 46 is provided to remove excess by-products, such as propane and other gases, from the system. The crude aldehyde is recovered via line 41 and refined, as desired.

If desired, vent line 24 and/or vent line 17 in the primary system can be employed singularly, plurally or in conjunction with vent line 28 as the feed line for the decoupled system.

The primary and secondary reactors each contain, as will be appreciated, a solubilized rhodium catalyst composition comprising a solubilized rhodium-phosphorous complex catalyst, free phosphorous ligand and a solvent, e.g. aldehyde and/or aldehyde high boiling condensation by-products. The catalyst compositions may be the same or different in the two reactors as shown and discussed above.

It is a unique feature of this invention that the secondary decoupled reactor can employ partially deactivated catalyst. For example, it is known that, despite the obvious advantages of the above invention, during use the rhodium complex catalyst loses activity (i.e. becmes partially deactivated) and eventually, after prolonged use, the activity of the catalyst will have decreased to such a point that it is no longer economically desirable to operate the hydroformylation process, and the catalyst will have to be discharged and replaced with fresh catalyst. Accordingly, due to the high cost of rhodium values, the ability to employ partially deactivated catalyst in the secondary, decoupled reactor, which catalyst might be so deactivated as not to be preferably employable in the primary reactor, is obviously of high benefit to the state of this art.

It will be understood that for the purposes of this invention more than one reactor can be employed in series or in parallel in both the primary or secondary systems of this invention.

In a second preferred embodiment employing a primary reactor having a gas recycle, one or a series of reactors operates in parallel with individual feeds and effluent lins from a common inlet feed and a common effluent line. A gaseous effluent stream from the reactor(s) is conducted to a product separation recovery zone in which aldehyde product is condensed and recovered with other higher boiling aldehyde condensation products. A portion of the uncondensed gaseous effluent stream which includes unreacted olefin, syn gas, inerts and by-product is compressed and recycled to the process. Additional make-up olefin and syn gas are added, as required.

Saturated olefinic by-product, such as propane, tends to build up in the system. Accordingly, the nonrecycled portion of the uncondensed gaseous effluent stream, which include, unreacted olefin, syn gas, inerts and by-product, is taken as a vent stream to remove such propane.

It should be understood from the previous discussion regarding the liquid recycle embodiment that the olefin starting material for the secondary decoupled process can be taken from any gaseous stream which would be vented from the primary process as off-gas. While such olefin starting material for the secondary decoupled process can be derived from any appropriate gas vent containing olefin (and incidental alkane by-products) taken from any suitable location in the primary reaction system, it is preferred to employ the vent stream taken from the gas recycle stream as the feed for the secondary decoupled rhodium catalyzed hydroformylation process. The olefin containing vent gas is admixed with make-up quantities of syn gas and that feed is introduced into the secondary decoupled reactor. As noted above, make-up quantities of olefin need not be, and preferably are not, added to the secondary decoupled reactor.

The process carried out in the secondary decoupled system, as set forth previously, can employ the same or different reaction conditions as utilized in the primary hydroformylation process discussed above. A liquid recycle or gas recycle can be emloyed in the secondary process in accordance with the same or different conditions as noted hereinbefore.

The primary and secondary reactors each contain, as will be appreciated, a solubilized rhodium catalyst composition comprising a solubilized rhodium-phosphorous complex catalyst, free phosphorous ligand and a solvent, e.g. aldehyde and/or aldehyde high boiling condensation by-products. The catalyst compositions may be the same or different in the primary or secondary reactors.

It is a unique feature of this invention that the secondary decoupled reactor can employ partially deactivated catalyst as discussed before. It will also be understood that more than one reactor can be employed in series or in parallel in the primary or secondary systems of this embodiment.

Accordingly, this embodiment can be further illustrated by reference to FIG. 2, which schematically shows a diagrammatic flow sheet suitable for practicing this invention.

Figure 2:
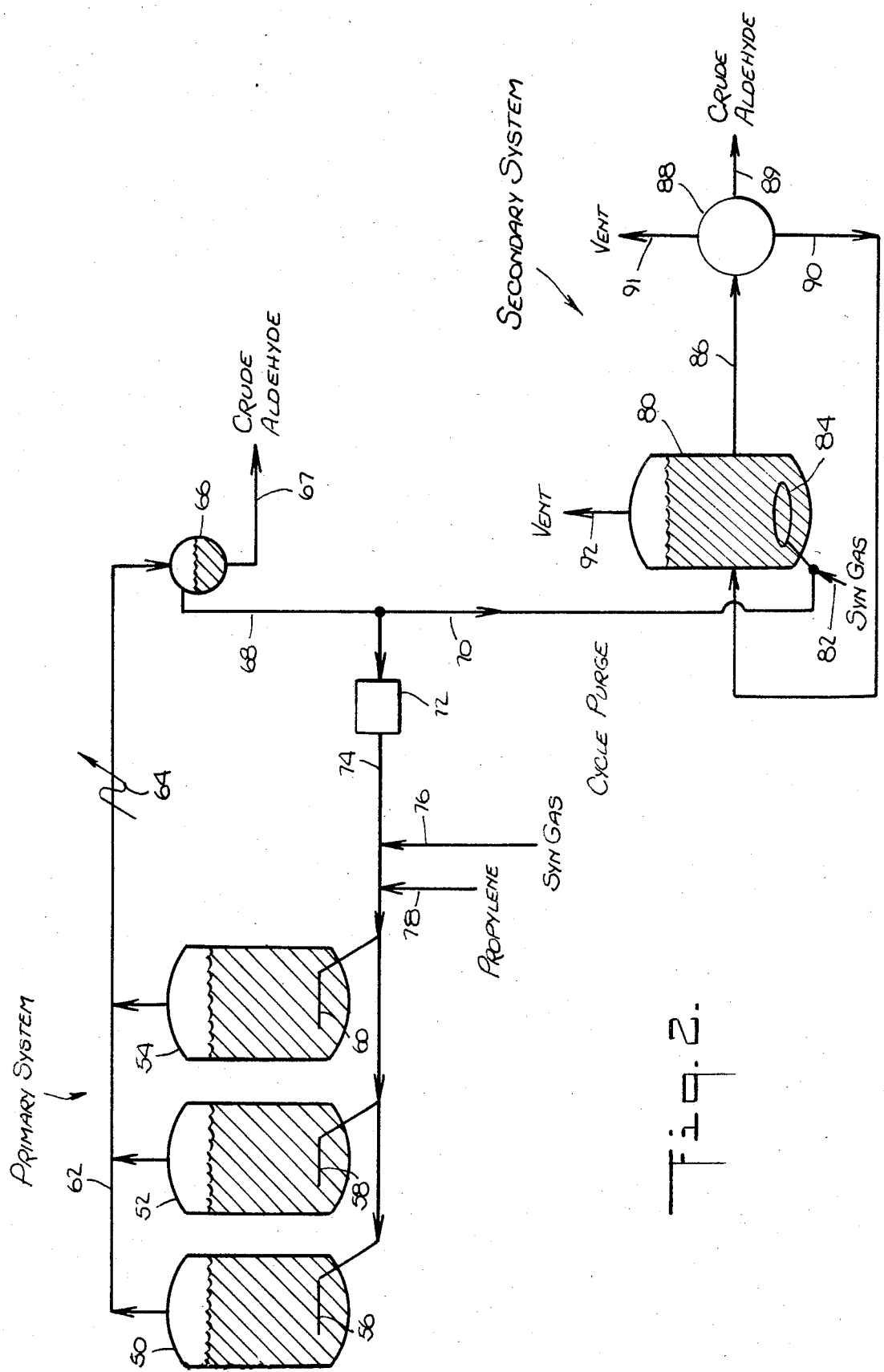
FIG. 2 is a schematic flow diagram illustrating operation of three primary single stage gas recycle LPO reactors in parallel in which a gas vent stream acts as a feed to a secondary decoupled LPO process employing a single stage reactor with a liquid recycle.

Referring to FIG. 2 in which a process for converting propylene to butyraldehyde is illustrated, three LPO process reactors 50, 52 and 54 are provided in parallel. Each reactor has a sparger 56, 58 and 60 having a plurality of holes therein to provide gas dispersion to the reactor.

Each reactor also contains an impeller (not shown), which is employed to mix the reactor contents and an internal or external cooler (not shown), which is employed to help control reaction temperature. Vaporous product effluent from the reactors is removed via line 62 and passed to a condenser 64 to condense aldehyde product from the recycle gases. A separator-catchpot 66 is used to separate the condensed crude aldehyde product from the noncondensed recycle gases. Condensed aldehyde liquid is recovered from separation-catchpot 66 via line 67 and refined, as desired. Recycle gases are removed by line 68 from which a purge or vent is taken through line 70. The remaining recycle gases are cycled through compressor 72 to line 74 into which is fed make-up reactant feeds through lines 76 (syn gas) and 78 (propylene). The enriched feed is then supplied to reactors 50, 52 and 54.

The unreacted olefin-containing gas in vent line 70 is then introduced to secondary decoupled reactor 80 together with make-up syn gas from make-up feed line 82 via sparger 84. Reactor 80 is also equipped with an agitator and means for temperature control. A liquid hydroformylation reaction catalyst stream is removed from reactor 80 via line 86 to a product recovery zone 88, wherein aldehyde product is vaporized and condensed. Crude condensed aldehyde product is obtained via line 89 and refined, as desired.

Vaporized light gaseous materials can be vented via line 91 or recycled, to the reactor, if desired. The non-volatilized concentrated catalyst-containing solution is recycled via line 90 to reactor 80. A purge or vent line 92 is provided in the headspace of the secondary reactor 80 to serve as a means for controlling internal pressure build-up in the reactor.

Again, the concept of the decoupled series mode of this invention is applicable to any combination of reactor systems whether they be liquid recycle-liquid recycle; gas recycle-gas recycle; liquid recycle-gas recycle or gas recycle-liquid recycle. It is also possible to employ a heterogeneous rhodium catalyst system on a solid support in the secondary decoupled reactor.

In general the olefin efficiency provided by this invention improves as the secondary decoupled reactor catalyst volume increases relative to the primary reactor catalyst volume. More catalyst is required as the secondary decoupled reactor catalyst volume is increased. For most purposes the secondary reactor is no larger in catalyst volume than the primary reactor and may be quite small relative to the primary reactor. Usually the ratio of secondary reactor system catalyst volume to primary reactor system catalyst volume is from about 0.05:1 to 1:1. Preferred ratios are from 0.1:1 to 1:1 and, most preferably, about 0.33:1 to 1:1.

The following examples serve to illustrate the practice of this invention and not to limit it. Mole efficiency as employed herein is defined as the number of moles of aldehyde product recovered divided by number of moles of reactant fed and the result multiplied by 100.

EXAMPLE 1

Computer simulation experiments were conducted in order to demonstrate the olefin efficiency improvements of the subject invention as follows:

Three stainless steel cylindrical reactors in the primary reaction system as characterized in FIG. 2 are operated in parallel employing a gas recycle procedure. A liquid recycle reactor is employed in the secondary decoupled reactor system. Each reactor in both the primary and secondary system contains a solution of a solubilized rhodium-triphenylphosphine (TPP) complex catalyst in butyraldehyde, free triphenylphosphine ligand and butyraldehyde trimers. Butyraldehyde product is produced from the hydroformylation of propylene with syn gas.

The olefin feed for the secondary decoupled system is the vent gas stream in line 70 from the primary system.

The ratio of catalyst volume in the secondary decoupled reactor to catalyst volume in the primary system (as the sum of the three reactors) is 0.1:1.

The conditions of the reactions using the process design of FIG. 2 are set forth in Table 1 as follows:

TABLE 1

|  | Primary-Gas Recycle | Secondary-Liquid Recycle |
|---|---|---|
| Reaction temperature, °C. | 95 | 90 |
| Reaction pressure, psia | 255 | 245 |
| Rhodium concentration, ppm | 300 | 265 |
| TPP concentration, wt % | 12 | 11.9 |

The flows in the reaction lines are as set forth in the following Table 2:

TABLE 2

| | | Mol % | | | | | |
|---|---|---|---|---|---|---|---|
| Line | Flow, g mol/hr | Propylene | Hydrogen | Carbon Monoxide | Butyraldehyde | Propane | Methane[1]/Trimer[2] |
| 78 | 1.800 | 98.00 | 0.00 | 0.00 | 0.00 | 2.00 | 0.00/0.00 |
| 76 | 3.362 | 0.00 | 51.72 | 47.88 | 0.00 | 0.00 | 0.40/0.00 |
| 67 | 1.600 | 0.19 | 0.00 | 0.00 | 99.45 | 0.06 | 0.00/0.30 |
| 70 | 0.321 | 36.13 | 29.43 | 3.35 | 1.65 | 24.77 | 4.73/0.00 |
| 82 | 0.198 | 0.00 | 51.72 | 47.88 | 0.00 | 0.00 | 0.40/0.00 |
| 92 | 0.186 | 7.58 | 55.74 | 7.68 | 2.17 | 26.36 | 0.47/0.00 |
| (89 + 91) | 0.148 | 6.55 | 10.30 | 0.09 | 61.43 | 21.40 | 0.01/0.09 |

[1]methane inert impurity from syn gas
[2]high boiling butyraldehyde by-product

The efficiency of the decoupled series mode of the invention as conducted above was compared to the efficiency of a simulated conventional gas recycle primary reactor system employing three reactors with the reaction catalyst, reaction conditions and flows simulated in the same manner as above, but without use of the secondary decoupled system. The gases in line 70 in this comparison test were wasted. The results were as follows as set forth in Table 3.

TABLE 3

| | Efficiency, Mol % | |
|---|---|---|
| | Decoupled Series Mode of Invention | Conventional System |
| Propylene | 94.0 | 89.2 |
| Carbon Monoxide | 99.2 | 92.0 |
| Hydrogen | 94.0 | 85.2 |

Thus, it is seen that the mole efficiency based on propylene of the present invention process is increased in this Example by almost 5 percent as compared to a conventional system. It will be appreciated that this unexpectedly enhanced increase in efficiency can result in major economic benefits, since hundreds of millions of pounds of aldehyde product are produced annually employing rhodium-catalyzed hydroformylation processes.

EXAMPLE 2

A computer simulation experiment was conducted in accordance with the FIG. 1 process in which a primary reactor employing liquid recycle is connected to a secondary decoupled reactor employing gas recycle. Each reactor in both the primary and secondary system contains a solution of a solubilized rhodium-TPP complex catalyst in butyraldehyde, free triphenylphosphine ligand and butyraldehyde trimers. Butyraldehyde is produced from the hydroformylation of propylene with syn gas.

The ratio of catalyst volume in the secondary decoupled reactor to catalyst volume in the primary reactor is 0.65 to 1.0.

The conditions of the reaction using the process design of FIG. 1 are set forth in Table 4 as follows:

TABLE 4

|  | Primary-Liquid Recycle | Secondary-Gas Recycle |
|---|---|---|
| Reaction Temperature, °C. | 90 | 110 |
| Reaction pressure, psia | 275 | 245 |
| Rhodium concentration, ppm | 267 | 332 |
| TPP concentration, wt % | 12.0 | 10.3 |

The flows in the reaction lines are as set forth in Table 5 as follows:

TABLE 5

| Line | Flow g mol/hr | Mol % | | | | | | |
|---|---|---|---|---|---|---|---|---|
|  |  | Propylene | Hydrogen | Carbon Monoxide | Butyraldehyde | Propane | Methane | Trimer |
| 13 | 7.725 | 34.33 | 32.39 | 30.37 | 0.00 | 2.59 | 0.42 | 0.00 |
| 17 | 0.941 | 51.40 | 1.66 | 0.43 | 5.02 | 41.10 | 0.31 | 0.00 |
| 24 | 0.346 | 48.50 | 0.00 | 0.00 | 17.80 | 33.70 | 0.00 | 0.00 |
| 25 | 2.512 | 6.60 | 0.00 | 0.00 | 89.54 | 3.66 | 0.00 | 0.08 |
| 28 | 0.783 | 36.60 | 17.84 | 3.64 | 7.10 | 30.70 | 4.14 | 0.00 |
| 36 | 0.488 | 0.00 | 50.97 | 48.02 | 0.00 | 0.00 | 1.01 | 0.00 |
| 41 | 0.293 | 0.28 | 0.00 | 0.00 | 96.89 | 0.69 | 0.00 | 3.13 |
| 46 | 0.481 | 6.76 | 27.72 | 4.21 | 1.70 | 51.86 | 7.76 | 0.00 |

The efficiency of the decoupled series mode of the invention as conducted above for a primary liquid recycle system and a secondary decoupled gas recycle system was compared to the efficiency of a simulated conventional liquid recycle primary reactor system with the reaction catalyst, reaction conditions and flows simulated in the same manner as above, but without use of the secondary decoupled system. The gases in line 28 in this comparison test were wasted. The results were as follows as set forth in Table 6:

TABLE 6

| Efficiency Mol % | Decoupled Series System | Conventional System |
|---|---|---|
| Propylene | 95.7 | 85.2 |
| Carbon Monoxide | 98.5 | 96.3 |
| Hydrogen | 92.6 | 90.5 |

It will be seen that the mole efficiency based on propylene of this embodiment of the present invention is increased over 10% as compared to the comparative conventional system.

EXAMPLE 3

The experiment of Example 2 was repeated except that the aldehyde production rate of both the decoupled series and the comparative conventional systems was increased by increasing propylene feed rate in each primary reactor by 42%. The comparative efficiency of the process of Example 2 is compared to the efficiency of the process of Example 3 in Table 7 as follows:

TABLE 7

| Constituents | Decoupled Series System | | | Conventional System | | |
|---|---|---|---|---|---|---|
|  | Ex. 2 | Ex. 3 | Change | Ex. 2 | Ex. 3 | Change |
| Propylene (mol % efficiency) | 95.7 | 94.3 | −1.4 | 85.2 | 77.4 | −7.8 |
| Carbon Monoxide (mol % efficiency) | 98.5 | 98.4 | −0.1 | 96.3 | 94.9 | −1.4 |
| Hydrogen (mol % efficiency) | 92.6 | 92.6 | 0.0 | 90.5 | 89.4 | −1.1 |

In general, as propylene feed rate to a system is increased, the efficiency of the process is correspondingly reduced. The above comparative results illustrate that by employing the decoupled series mode of the present invention, increased propylene feed rate results in unexpectedly superior propylene mol efficiency as compared to the propylene mol efficiency of a comparative conventional system.

The process simulation programs simulated LPO processes by iterative solution of the material balance equations which describe the process. The programs have been calibrated against other actual runs and have proved reliable predictors of efficiency.

Heretofore, when olefin feed rate in conventional rhodium-catalyzed hydroformylation processes was increased, significant decreases in olefin mole efficiency were noted. It is an important feature of the present invention, as demonstrated by the above results, that increased olefin feed rates result in relatively minor reductions in olefin mole efficiency. As shown by the results in Table 7, specifically, a 42% increase in propylene feed rate produced a 1.4% reduction in efficiency for the decoupled series system, as compared to a 7.8% reduction in efficiency for a conventional liquid recycle process. This feature of the present invention permits larger increases in olefin feed rates to be employed to meet changing needs without suffering undue losses in olefin mole efficiency for the instant process.

In addition, the above test results show that equivalent aldehyde production rate increases can be achieved by employing smaller increases in olefin feed rate for the decoupled series system as compared to the olefin feed rate increase required for the conventional comparative system.

For example, as illustrated in Table 7 for the decoupled series system, 95.7 moles of butyraldehyde was recovered for each 100 moles of propylene fed in the Example 2 simulation experiment. In the Example 3 decoupled series simulation experiment 133.9 moles of butyraldehyde were recovered for each 142 moles of propylene fed for a mole efficiency of 94.3%; i.e.

[(100 moles propylene feed (Ex. 2) +
    42 moles increased propylene feed) =
    142 moles propylene feed (Ex. 3) ×

$$0.943 \frac{\text{(moles butyraldehyde recovered)}}{\text{(moles propylene feed)}} \text{ (Ex. 3)} =$$

133.9 moles butyraldehyde].

This corresponds to an increase in butyraldehyde produced of 39.9%, $$\left[ \frac{(133.9 - 95.7)}{(95.7)} \times 100\% \right]$$

for the decoupled series system.

Likewise, it can be calculated that the percent increase in butyraldehyde produced by the conventional system, based on the Table 7 results, is only 29%.

Therefore, the decoupled series system produced 37.6% more aldehyde than the conventional system from an equivalent increase in olefin feed.

As seen above, in each experiment employing the decoupled series mode process of the invention, olefin efficiency was significantly increased wherein the olefin feed to the secondary system is taken solely from a vent stream from the primary system.

EXAMPLE 4

In order to further demonstrate the olefin efficiency improvement of the process of the present invention, the following data is given from a commercial decoupled series system of the invention which was actually operated in accordance with the system set forth in FIG. 1 in which vent stream 28 of the primary liquid recycle reactor was employed as the olefin feed to a decoupled secondary reactor employing a gas recycle. Each reactor in both the primary and secondary system contained a solution of a solubilized rhodium-TPP complex catalyst in butyraldehyde, free triphenylphosphine ligand and butyraldehyde trimers. In the process propylene was hydroformylated with syn gas to butyraldehyde. The ratio of catalyst volume in the secondary decoupled reactor to catalyst volume in the primary reactor was 0.53:1.0.

The conditions of the reaction were as set forth in Table 8 as follows:

TABLE 8

| | Decoupled Series Mode | |
|---|---|---|
| | Primary-Liquid Recycle Reactor | Secondary-Gas Recycle Reactor |
| Hydrogen, psia | 34.9 | 36.4 |
| Carbon Monoxide, psia | 7.0 | 4.2 |
| Propylene, psia | 109.9 | 16.8 |
| Reactor pressure, psia | 274.7 | 234.7 |
| Reaction temperature, °C. | 85.0 | 85.0 |
| Butyraldehyde produced, g.mole/L/hr | 1.9 | 0.14 |
| Rhodium concentration, ppm | 242.0 | 257.0 |
| TPP Concentration, wt. % | 11.9 | 15.0 |

After about 40 days efficiency of the process was found to be 96.9 mol percent based on conversion of propylene to butyraldehyde.

When a conventional primary reactor with a gas recycle was operated generally in accordance with the reaction conditions in the primary reactor in the decoupled series mode illustrated in this Example, the conversion efficiency for the conventional system was only on the order of 92 mol percent.

The results further demonstrate that operating the inventive process with a single olefin feed to the secondary reactor from a primary reactor provides highly effective hydroformylations using the decoupled series mode of the invention.

We claim:

1. In a primary liquid recycle or gas recycle rhodium-catalyzed hydroformylation process for producing aldehydes, wherein an olefin, carbon monoxide and hydrogen are reacted in the presence of a solubilized rhodium-phosphorus complex catalyst, free phosphorus ligand and higher boiling aldehyde condensation by-products to produce an aldehyde product, wherein a gaseous effluent comprising unreacted olefin and any of said aldehyde product, hydrogen, carbn monoxide and an alkane by-product is vented from the process, the improvement which comprises: conducting a decoupled secondary liquid recycle or gas recycle rhodium-catalyzed hydroformylation process conjointly with said primary process, wherein said gaseous effluent together with make-up carbon monoxide and hydrogen is employed as the reactant feed to the secondary process.

2. The process of claim 1 wherein the primary rhodium-catalyzed hydroformylation process comprises a liquid recycle process and the improvement comprises employing as the reactant feed to the decoupled secondary process a gaseous effluent containing unreacted olefin vented solely from the headspace of the primary reactor together with make-up quantities of carbon monoxide and hydrogen.

3. The process of claim 2 wherein the decoupled secondary rhodium-catalyzed hydroformylation process comprises a gas recycle process.

4. The process of claim 3 wherein the free phosphorus ligand and phosphorus ligand of the rhodium-phosphorus complex catalyst is a triorganophosphine compound.

5. The process of claim 4 wherein the triorganophosphine compound is triphenylphosphine.

6. The process of claim 3 wherein make-up olefin is not added to the decoupled secondary process.

7. The process of claim 1 wherein the primary rhodium-catalyzed hydroformylation process comprises a gas recycle process and the improvement comprises employing as the reactant feed to the decoupled secondary process, a gaseous effluent containing unreacted olefin vented solely from the gaseous recycle stream from the primary process together with make-up quantities of carbon monoxide and hydrogen.

8. The process of claim 7 wherein the decoupled secondary rhodium-catalyzed hydroformylation process comprises a liquid recycle process.

9. The process of claim 8 wherein the free phosphorus ligand and phosphorus ligand of the rhodium-phosphorus complex catalyst is a triorganophosphine compound.

10. The process of claim 9 wherein the triorganophosphine compound is triphenylphosphine.

11. The process of claim 8 wherein make-up olefin is not added to the decoupled secondary process.

12. The process of claim 1 in which the ratio of secondary decoupled reactor catalyst volume to primary reactor catalyst volume is from about 0.05:1 to 1:1.

13. The process of claim 1 in which the ratio of secondary decoupled reactor catalyst volume to primary reactor catalyst volume is from about 0.1:1 to 1:1.

14. The process of claim 1 in which the phosphorus ligand is a triorganophosphine compound.

15. The process of claim 1 in which the phosphorus ligand is triphenylphosphine.

16. The process of claim 1 in which the hydroformylation reaction in the primary and secondary process is conducted at a reaction temperature from about 50° C. to 145° C.

17. The process of claim 16 in which the hydroformylation reaction temperature is from about 75° C. to 115° C.

18. The process of claim 1 in which the rhodium concentration in the primary and secondary process is from about 10 to 700 ppm, calculated as free rhodium metal.

19. The process of claim 18 in which the rhodium concentration is from about 25 to 500 ppm rhodium, calculated as free rhodium metal.

20. The process of claim 1 in which from about 1 to 300 mols of free ligand are present per mole of rhodium.

21. The process of claim 1 in which the total pressure of olefin, carbon monoxide and hydrogen in each of the primary and decoupled secondary processes is less than about 450 psia and the molar ratio of hydrogen to carbon monoxide is from about 1:10 to 100:1.

22. The process of claim 21 in which the total pressure of olefin, carbon monoxide and hydrogen is less than about 350 psia and the molar ratio of hydrogen to carbon monoxide is from about 1:1 to 50:1.

23. The process of claim 1 in which the ratio of said aldehyde product to said high boiling aldehyde condensation by-products in the hydroformylation reaction zone of each reactor is from about 1:4 to 20:1 in the hydroformylation process.

24. The process of claim 1 in which the olefin has from 2 to 5 carbon atoms.

* * * * *